United States Patent [19]

Gutcho et al.

[11] 4,120,945

[45] Oct. 17, 1978

[54] SUBSTRATE COATED WITH RECEPTOR AND LABELED LIGAND FOR ASSAYS

[75] Inventors: Sidney Gutcho, Monsey; Henry McCarter, Pine Island, both of N.Y.

[73] Assignee: Becton, Dickinson & Company, Rutherford, N.J.

[21] Appl. No.: 702,691

[22] Filed: Jul. 6, 1976

[51] Int. Cl.² .................... G01N 33/16; G01N 23/00; G01N 31/06
[52] U.S. Cl. ...................................... 424/1; 23/230 B; 23/230.6; 424/12; 422/57
[58] Field of Search ................. 23/230 B, 230.6, 259, 23/253 TP; 424/1, 12

[56] References Cited

U.S. PATENT DOCUMENTS

| | | | |
|---|---|---|---|
| 3,646,346 | 2/1972 | Catt | 23/230 B X |
| 3,790,663 | 2/1974 | Garrison | 424/1 X |
| 3,867,517 | 2/1975 | Ling | 23/230 B X |
| 4,012,494 | 3/1977 | Ling | 23/230 B |
| 4,017,597 | 4/1977 | Reynolds | 23/230 B X |

*Primary Examiner*—Sidney Marantz
*Attorney, Agent, or Firm*—Marn & Jangarathis

[57] ABSTRACT

Solid substrate is coated with a receptor, with a limited portion of the receptor being reversibly coated with a labeled form of a ligand to be assayed, whereby during an assay procedure the labeled form of the ligand is free to re-equilibrate with the receptor in competition with the ligand to be assayed.

19 Claims, No Drawings

SUBSTRATE COATED WITH RECEPTOR AND LABELED LIGAND FOR ASSAYS

This invention relates to the assay of ligands, and more particularly, to a new and improved article and process for assaying for ligands.

The present procedure for assaying for ligands is based on the competition between a labeled form of a ligand and the ligand for a limited number of sites on a receptor for the ligand. In brief, a known quantity of the labeled form of the ligand, a sample containing an unknown quantity of ligand and a known quantity of receptor for the ligand are combined, and the percentage of the labeled form of the ligand bound to the receptor will depend upon the quantity of ligand in the sample. After the receptor, including bound ligand, is separated from the sample the amount of the labeled form of the ligand bound to the receptor or remaining in the sample is determined and compared with a standard curve to determine the quantity of ligand which was present in the sample.

In order to facilitate separation of the receptor from the sample, in many cases, the receptor is bound to a solid phase, in the form of a tube, insoluble particles or the like, whereby the receptor including bound ligand can be easily separated from a sample for making the determination as to the quantity of labeled ligand which is either bound to the receptor or remains free in the sample.

The present invention is directed to an improvement in the article and procedures for effecting an assay in which the receptor is bound to an insoluble solid phase.

In accordance with the present invention there is provided an article for the assay of a ligand which is a solid substrate, having a receptor for both the ligand to be assayed and a labeled form of the ligand to be assayed thereon, with the labeled form of the ligand being reversibly coated on the surface of the receptor, whereby during an assay the labeled ligand is removed from the receptor for re-equilibration with the receptor, in competition with the ligand to be assayed. In this manner, there is provided an article containing both a receptor and a labeled form of the ligand to be assayed, whereby an assay can be effected by equilibrating a sample containing the ligand to be assayed with the solid substrate including the receptor and the labeled form of the ligand, thereby eliminating the necessity for separate addition of labeled ligand and sample during an assay.

The ligand which can be coated on the receptor, in labeled form, is any one of a wide variety of ligands for which an appropriate receptor can be found, such as (1) antigens, which when introduced into the blood stream of a vertebrate, result in the formation of antibodies; (2) haptens, which when bound to an antigenic carrier and introduced into the blood stream of a vertebrate, produce antibodies specific for the hapten, or (3) ligands which have naturally occuring receptors which can be isolated in a form specific for the ligand. It is to be understood that a ligand can have naturally occuring receptors and also function as a hapten when bound to a protein.

As representative examples of ligands to which the present invention is applicable, there may be mentioned: polypeptides, nucleotides, nucleosides and proteins, such as ACTH, oxytocin, lutenizing hormone, insulin, proinsulin, Bence-Jones protein, chorionic gonadotropin, pituitary gonadotropin, growth hormone, renin, thyroxine binding globulin, bradykinin, angiotensin, follicle stimulating hormone; cyclic AMP; chalylglglycine, cyclic GMP, etc.; steroids, including: estrogens, gestogens, androgens, adrenocortical hormones, bile acids, cardiotonic glycosides, aglycones as well as saponins. As specific examples, these may be mentioned: thyroxine, triiodothyronine, testosterone, androsterone, equilenin, estrone, estriol, progesterone, pregnenolone, 17-hydroxydioxycorticosterone (compound S), deoxycorticoserone, cortisone, corticosterone, cortisol, aldosterone, digoxin, digitoxin, etc.; vitamins, such as vitamin A, folic acid, the B vitamin group, vitamin C, the D vitamins, and vitamins E and K; and miscellaneous ligands, such as, antigens for Viral Hepatitis A and B, Rubella, Herpes Simplex, α-fetoprotein, etc.

The above substances are only representative, and it is understood that such substances can be used as appropriate analogs and the term labeled form of the ligand includes such analogs.

The ligand is coated on the antibody in labeled form; ie., the ligand coated on the antibody applied to a solid support contains a "label", "tag" or "tracer", (such terms are interchangeably used in the art) which can be a radioisotope, an enzyme, a fluorescent material, etc. The use of such labels or tags and the procedures for preparing a ligand containing such label, tag or tracer are well known in the art and no further details in this respect are needed for a complete understanding of the invention. The preferred labeled ligand is radiolabeled, and as known in the art, such radioactive isotope is generally tritium or one of the radioisotopes of iodine.

The solid material on which the antibody is coated may be any one of a wide variety of solid materials. As known in the art, such materials include suitable polymers, such as, polystyrene, polyethylene, polypropylene, polytetrafluoroethylene, polyamides, polyacrylamides, etc.; glass, bacterial cells; ion exchange resins; etc. Such solid carriers are known in the art and no further details in this respect are deemed necessary for a full understanding of the invention.

As known in the art, the receptor is coated on the solid phase, which can be in particulate form, sheet form or in the form of a tube, with a tube being particularly preferred. The antibody adheres to the solid phase either by adsorption or by suitable covalent coupling to the solid phase, all of which procedures are known in the art. The preferred solid phase is a plastic tube and in particular a tube formed of polystyrene.

It has been found that a superior product is formed if the antibody is coated onto a solid substrate to which the receptor adheres by adsorption by a technique in which the biologically receptive sites are blocked with a blocking agent whereby the receptor is oriented with respect to the surface.

In accordance with such a technique, a receptor is coated on a plastic substrate in the presence of a deaggregation agent for the receptor and a blocking agent for the ligand receptor sites in order to effect adherence of the receptor to the plastic substrate at other than the receptor sites.

More particularly, the blocking agent is a substance which has a limited cross-reactivity with the receptor in order to effect blocking of the ligand receptor sites to thereby prevent adherence of the receptor to the plastic at the ligand receptor sites, while also permitting subsequent binding of a ligand to the receptor. In general, the substance employed as a blocking agent for the ligand receptor sites has a cross-reactivity with the receptor of from about 0.001 to about 5%, and preferably from about 0.001 to about 1%. The upper limit of the cross-reactivity insures that in a subsequent assay the blocking agent can be displaced by the ligand to be assayed whereby there can be competitive binding at the receptor sites. As should be apparent, the substance employed as a blocking agent should have an affinity for the plastic surface which is lower than the affinity of the receptor for the plastic surface in order to permit orientation of the receptor on the plastic. The substance employed as a blocking agent is preferably hydrophilic; however, it is to be understood that non-hydrophilic substances can also be employed.

As representative examples of suitable blocking agents, there may be mentioned: cardiac glycosides, such as, ouabain, gitoxin, gitaloxin, acetyl strophanthidin, etc.; steroids, such as progesterone testesterone, cortisol, etc.

The selection of a suitable agent for blocking the receptor sites is deemed to be within the scope of those skilled in the art from the teachings herein.

The coating of antibody on the plastic substrate is also effected in the presence of a deaggregating agent for the receptor in order to prevent adherence to the plastic substrate in clumps or aggregates, which would limit the availability of receptor sites in the subsequent assay. The deaggregating agent may be one of a wide variety of such agents which are used in the art, and as representative examples of such agents, there may be mentioned: amino acids, such as, glycine, lysine, etc.; urea; guanidine; soluble inorganic salts; in particular, calcium salts, and the like. The selection of a suitable deaggregating agent is deemed to be within the scope of those skilled in the art from the teachings herein.

The blocking agent is employed in an amount effective for blocking the receptor sites of the receptor for the ligand, which will vary with the amount of receptor and the particular receptor employed. In general, the blocking agent is employed in an amount of from 0.0001 to 0.01%, preferably from 0.0005 to 0.005%, all weight percent of solution. Similarly, the amount of deaggregating agent employed is dependent on the receptor and amount thereof, with the deaggregating agent generally being employed in an amount of from 0.01 M to 0.9 M, preferably from 0.25M to 0.35M. The amount of blocking agent and deaggregating agent to be employed is deemed to be within the scope of those skilled in the art from the teachings herein. The receptor coated substrate is generally further treated with a protein containing buffer to reduce or eliminate non-specific binding in the assay.

It has been found that by coating the plastic substrate with antibody in the presence of both a blocking agent and a deaggregating agent, the amount of receptor required for the coating is significantly lower than that required in prior art techniques. It has also been found that the use of such lower amounts of antibody facilitates re-equilibration of the tracer.

The antibody coated on the solid surface is then coated with the labeled ligand. The labeled ligand is applied to only a portion of the receptor surface. In general, the labeled ligand is applied to less than 50% of the receptor surface, with the ligand generally being applied to at least 0.5% of the receptor surface. Most generally, the receptor is applied to from 5 to 25% of the receptor surface. It has been found that re-equilibration of the labeled receptor is facilitated by limiting the application thereof to only a portion of the receptor surface. Such a result can be readily achieved by limiting the surface contact area between receptor and labeled ligand in coating the receptor with the labeled ligand. Thus, for example, where an antibody coated plastic tube is employed, the surface area of antibody coated with labeled ligand is limited by placing only a small volume of the labeled ligand solution in the tube whereby only the bottom portion of the tube is contacted with the labeled ligand and only the bottom portion of the receptor coated on the tube is coated with labeled ligand, with the upper portion of the coated receptor being free of labeled ligand. In conducting the assay in the tube, the labeled ligand is removed from the coated receptor and is free to re-equilibrate with the coated receptor. It has been found that notwithstanding the fact that the labeled ligand has been coated on only the lower portion of the tube, upon completion of the assay, the labeled ligand is evenly distributed over the entire portion of the coated receptor.

The labeled ligand is applied to the receptor as an unbuffered water solution, preferably distilled water, thereby eliminating the possibility of a remaining residue upon drying of the tube.

The labeled form of the ligand may be applied to the receptor coated solid substrate at room temperature; however, higher and lower temperatures could be employed, with it being understood that the temperature employed is one which does not adversely affect the ligand or receptor. Thus, there is provided a solid substrate which includes an appropriate receptor and only the labeled form of a ligand to be assayed, with the labeled form being free to re-equilibrate with the receptor in competition with the ligand to be assayed.

The solid substrate coated with antibody and having a small portion of the surface area of the antibody coated with a labeled form of a ligand to be assayed may now be employed for assays by procedures known in the art, except that only a sample containing the ligand to be assayed need be added to the system.

Thus, if the labeled form of the ligand is radiolabeled, the presence of ligand in a sample is determined by a radioimmunoassay, with the radiolabled form of the ligand being removed from the antibody and re-equilibrating with the antibody in an amount dependent upon the quantity of unlabeled ligand to be assayed in the sample. The amount of the radiolabeled form of the ligand present on the solid substrate or in the solution is determined by a suitable counter, as known in the art.

Similarly, if the labeled form of the ligand is enzyme labeled, the presence of ligand in a sample is determined by an enzyme amplification procedure as known in the art.

The present invention will be further described by reference to the following examples; however, the scope of the invention is not to be limited thereby.

EXAMPLE I

Digoxin antibody, elicited in sheep with a digoxin human serum albumin conjugate, in an aqueous buffer solution [0.05M carbonate/bicarbonate, pH 9.6, 0.3M glycine, 0.001% ouabain and 0.005% chloramphenicol] is added (1.0ml) to a polystyrene tube, at room temperature, and maintained at room temperature for 1 hour, followed by aspiration of the fluid from the tube. A buffer solution (0.1 M phosphate, pH 7.0, with 0.9% NaCl and 0.1% $NaN_3$), including 1 g of lysozyme per liter, is added to the tube and held at room temperature for about 10 minutes. The fluid is aspirated from the tube, and the tubes dried in vacuo at room temperature.

3-0-succinyl digoxigenin tyrosine [$^{125}$I] (U.S. Pat. No. 3,855,208) is diluted with distilled water to 15–20,000 cpm/50 µl and 50µl introduced into the antibody coated tube, followed by drying in vacuo to provide an antibody coated tube including tracer added thereto.

EXAMPLE II

The antibody coated tubes, including tracer, prepared as in Example I are used for digoxin assay as follows:

1. At room temperature, 50µl of Digoxin standard or Patient Sample and 1000µl of phosphate buffered saline (PBS) are pipetted into the tubes as follows:

| Tube No. | Digoxin in Standard (ng/ml) |
|---|---|
| 1, 2 | 0.0 |
| 3, 4 | 0.5 |
| 5, 6 | 1.0 |
| 7, 8 | 1.5 |
| 9, 10 | 2.0 |
| 11, 12 | 3.0 |
| 13, 14 | 5.0 |
| 15, 16 etc. | Patient Samples |

The tubes are incubated in a water bath at 37° C. for 60 minutes.

2. The liquor is aspirated from the tubes, followed by addition of 1.0–1.5 ml PBS and aspiration. The tubes now contain labeled and unlabeled digoxin bound to antibody.

3. The tubes are counted in sequence for 0.5–5 minutes with a gamma-counter and a standard curve is prepared which covers the range of 0.5–5 ng digoxin per ml of patient sample.

4. The digoxin concentration of the sample is obtained from the standard curve.

The present invention is particularly advantageous in that an assay may be effectively performed without the necessity for separate addition of tracer during the assay.

Numerous modifications and variations of the present invention are possible in light of the above teachings and, therefore, within the scope of the appended claims, the invention may be practiced otherwise than as particularly described.

What is claimed is:

1. An article for the assay of a ligand, comprising:
a solid, a receptor for both the ligand to be assayed and a labeled form of the ligand to be assayed on said solid, and a labeled form of the ligand to be assayed reversibly coated on at least 0.5% and no more than 25% of the surface of said receptor, whereby during an assay for the ligand, the labeled form of the ligand is removed from the receptor for re-equilibration with the receptor in competition with the ligand to be assayed.

2. The article of claim 1 wherein the receptor on the solid was applied in the presence of a blocking agent for the receptor and a deaggregating agent.

3. The article of claim 1 wherein the labeled form of the ligand to be assayed is reversibly coated on at least 0.5% of the receptor surface.

4. The article of claim 3 wherein the labeled form of the ligand is reversibly coated on no more than 25% of the receptor surface.

5. The article of claim 1 wherein the labeled form of the ligand is labeled with a radioactive isotope.

6. The article of claim 5 wherein the solid is a plastic.

7. The article of claim 6 wherein the solid plastic is in the form of a tube and only the bottom portion of the receptor on the tube has the labeled ligand coated thereon.

8. The article of claim 5 wherein the receptor is an antibody.

9. The article of claim 8 wherein the ligand to be assayed is digoxin and the labeled form of the ligand is a radiolabeled form of digoxigenin.

10. The article of claim 9 wherein the plastic is polystyrene.

11. The article of claim 10 wherein the labeled form of the ligand is 3-0-succinyl digoxigenin tyrosine [$^{125}$I].

12. In a process for the assay of a ligand, the improvement comprising:
equilibrating a sample including the ligand to be assayed with a solid phase having a receptor applied thereto and a labeled form of the ligand reversibly coated on at least 0.5% and no more than 25% of the surface of the receptor, whereby the labeled form of the ligand is removed from the receptor for re-equilibration with the receptor in competition with the ligand to be assayed.

13. The proess of claim 12 wherein the assay is a radioimmunoassay.

14. The process of claim 12 wherein the solid phase is in the form of a plastic tube.

15. The process of claim 12 wherein the labeled form of the ligand to be assayed is reversibly coated on only the bottom portion of the receptor surface on the plastic tube.

16. In a process for preparing an article for the assay of a ligand wherein a receptor for the ligand to be assayed is coated on a tube, the improvement comprising:
coating the labeled form of the ligand to be assayed on only the bottom portion of the receptor on the tube whereby the labeled form of the ligand is reversibly coated on at least 0.5% and no more than 25% of the surface of the receptor for re-equilibration with the receptor in competition with the ligand to be assayed.

17. The process of claim 16 wherein the coating is effected at room temperature.

18. The process of claim 17 wherein the ligand is labeled with a radioactive isotope.

19. The process of claim 18 wherein the receptor is an antibody.

* * * * *